United States Patent
Kasahara et al.

(10) Patent No.: US 6,777,518 B2
(45) Date of Patent: Aug. 17, 2004

(54) MEDICAL ADHESIVE COMPOSITION AND ADHESIVE TAPE OR SHEET USING THE COMPOSITION

(75) Inventors: Tsuyoshi Kasahara, Ibaraki (JP); Masayoshi Kuniya, Ibaraki (JP); Yasuyuki Sasaki, Ibaraki (JP); Takahisa Konishi, Ibaraki (JP)

(73) Assignee: Nitto Denko Corporation, Ibaraki (JP)

( * ) Notice: Subject to any disclaimer, the term of this patent is extended or adjusted under 35 U.S.C. 154(b) by 0 days.

(21) Appl. No.: 10/226,427

(22) Filed: Aug. 23, 2002

(65) Prior Publication Data

US 2003/0114621 A1 Jun. 19, 2003

(30) Foreign Application Priority Data

Aug. 23, 2001 (JP) .......................................... 2001-253579

(51) Int. Cl.$^7$ .............................................. C08F 220/68
(52) U.S. Cl. ...................... 526/318; 526/327; 526/328; 428/343; 428/355 AC
(58) Field of Search ................................ 526/318, 327, 526/328, 317, 321, 324; 428/343, 355 AC; 524/730, 731, 732

(56) References Cited

U.S. PATENT DOCUMENTS 5,648,166 A   7/1997   Dunshee 6,414,087 B1 * 7/2002 Hashemzadeh et al. ..... 525/191

FOREIGN PATENT DOCUMENTS

| DE | 4303616 C1 | 8/1994 |
| JP | 2002-53461 A | 2/2002 |
| WO | WO 91/1461 | * 10/1991 |
| WO | WO 91/14461 A1 | 10/1991 |

* cited by examiner

*Primary Examiner*—Robert D. Harlan
(74) *Attorney, Agent, or Firm*—Leydig, Voit & Mayer, Ltd.

(57) ABSTRACT

The present invention provides a medical adhesive composition containing a copolymer obtained by copolymerization of a monomer mixture containing an acrylic acid alkyl ester having C4–C12 alkyl group, a (meth)acrylic acid, and a methacrylic acid alkyl ester having C1–C4 alkyl group, which mixture is free of a multifunctional monomer having two or more unsaturated double bonds in a molecule, wherein the copolymer has a gel-sol ratio of 35:65 to 55:45 and a weight average molecular weight of the sol portion of 300,000 to 500,000, or a copolymer obtained by copolymerization of the above-mentioned monomer mixture and having a gel fraction of 35 to 55% and a swelling ratio of a gel portion of 50 to 90 times. The medical adhesive of the present invention is superior in the balance between adhesiveness and cohesiveness and can be preferably used for various medical adhesive tapes or sheets.

10 Claims, 1 Drawing Sheet

MEDICAL ADHESIVE COMPOSITION AND ADHESIVE TAPE OR SHEET USING THE COMPOSITION

FIELD OF THE INVENTION

The present invention relates to a medical adhesive composition used for adhesion to the skin in the medical and sanitary fields, and a medical adhesive tape or sheet prepared using this composition.

BACKGROUND ART

In general, a medical adhesive composition is applied to one side of a substrate as an adhesive layer, and used by adhesion to the skin in the form of a medical adhesive tape or sheet.

As a conventional medical adhesive composition, an acrylic adhesive containing an acrylic acid alkyl ester as a main component and a rubber adhesive containing a natural rubber and/or a synthetic rubber as a main component have been broadly used.

However, of the above-mentioned adhesive compositions, the rubber adhesives are relatively difficult to handle, because control of the adhesive property thereof is rather difficult, and particularly, natural rubber adhesives potentially cause expression of allergy and the like. Accordingly, acrylate adhesive compositions, which permit easy control of the adhesive property by adjusting composition ratios, amount of additives and the like, have been increasingly studied in recent years.

The present Applicant previously proposed a medical adhesive composition containing a copolymer obtained by copolymerizing a monomer mixture containing an acrylic acid alkyl ester having a C4–C12 alkyl group, (meth)acrylic acid, methacrylic acid alkyl ester having a C1–C4 alkyl group and a multifunctional monomer having two or more unsaturated double bonds in a molecule (JP-A-2002-53461).

The practical property requested of an adhesive layer is an adhesion force that prevents an adhesive tape or sheet from falling from the skin during use, that does not cause a physical pain upon peeling, and that does not easily cause skin irritation. It is of course necessary to have a cohesive force that does not leave an adhesive on the skin upon peeling. However, the adhesiveness and cohesiveness of an adhesive composition are subject to a cancel effect. Accordingly, a medical adhesive composition showing a superior balance between the adhesiveness and cohesiveness has been desired.

SUMMARY OF THE INVENTION

It is therefore an object of the present invention to provide an adhesive composition preferable for use as medical and sanitary materials (e.g. adhesive plaster, dressing, drape etc.), which shows a superior balance between an adhesiveness that permits sufficient fixing on the skin and a cohesiveness free of adhesive residue upon peeling, and an adhesive tape or sheet using this composition.

As a result of the intensive studies in an attempt to obtain an adhesive composition capable of satisfying the balance between the adhesiveness and cohesiveness practically necessary as a medical adhesive composition, the present inventors have found that a medical adhesive composition containing a copolymer obtained by copolymerization of a particular monomer mixture, or a monomer mixture obtained by removing a multifunctional monomer having two or more unsaturated double bonds in a molecule from a monomer mixture of the invention of JP-A-2002-53461, and having a particular scope of a gel-sol ratio and a weight average molecular weight of the sol portion is more superior in the balance between the adhesiveness and cohesiveness.

The present inventors have also took note of the correlation shown by the above-mentioned adhesive composition between a gel fraction and a swelling ratio of the gel portion, based on which also found that the above-mentioned adhesive composition having particular ranges of a gel fraction and a swelling ratio of the gel portion is more superior in the practical balance between the adhesiveness and cohesiveness.

Accordingly, the present invention provides the following.

(1) A medical adhesive composition comprising a copolymer obtained by copolymerizing a monomer mixture containing an acrylic acid alkyl ester having C4–C12 alkyl group, a (meth)acrylic acid, and a methacrylic acid alkyl ester having C1–C4 alkyl group, which mixture is free of a multifunctional monomer having two or more unsaturated double bonds in a molecule, wherein the copolymer has a gel-sol ratio of 35:65 to 55:45 and a weight average molecular weight of the sol portion of 300,000 to 500,000 (hereinafter to be also referred to as the present invention 1).

(2) A medical adhesive composition comprising a copolymer obtained by copolymerizing a monomer mixture containing an acrylic acid alkyl ester having C4–C12 alkyl group, a (meth)acrylic acid, and a methacrylic acid alkyl ester having C1–C4 alkyl group, which mixture is free of a multifunctional monomer having two or more unsaturated double bonds in a molecule, wherein the copolymer has a gel fraction of 35 to 55% and a swelling ratio of a gel portion of 50 to 90 times (hereinafter to be also referred to as the present invention 2).

(3) The medical adhesive composition of the above-mentioned (1) or (2), wherein the monomer mixture comprises 1 to 5 parts by weight of the (meth)acrylic acid and 3 to 20 parts by weight of the methacrylic acid alkyl ester, per 100 parts by weight of the acrylic acid alkyl ester.

(4) An adhesive tape or sheet having an adhesive layer made from the medical adhesive composition of any of the above-mentioned (1) to (3) formed on one surface of the substrate in a thickness of 10 to 100 µm.

PREFERRED EMBODIMENT OF THE INVENTION

Figure 1:
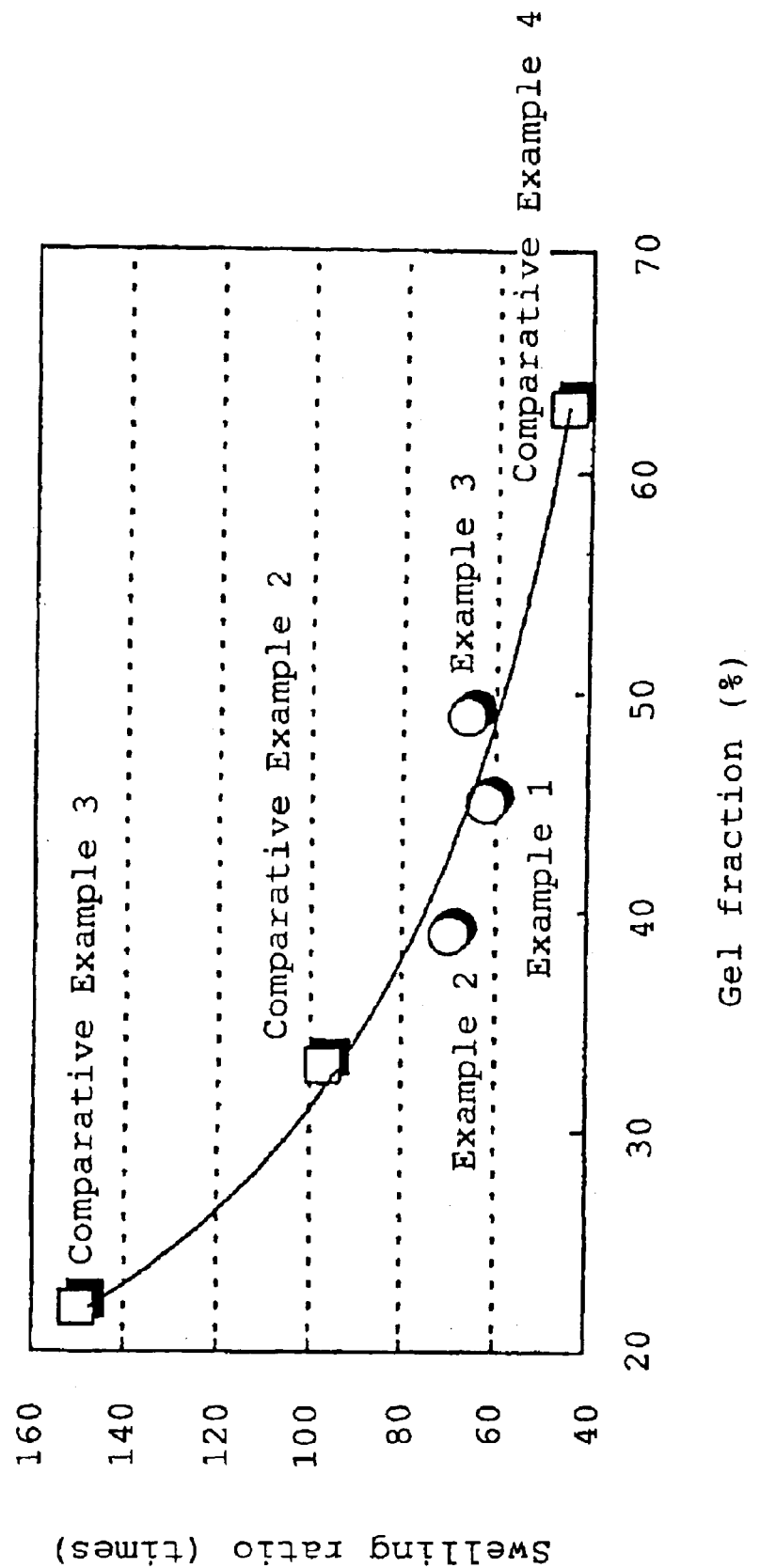
FIG. 1 shows a relationship between the gel fraction and the swelling ratio of the gel portion in the adhesive composition of the present invention.

In the following description, when the description is specifically identified to relate to the present invention 1 or the present invention 2, the feature characteristic of either invention is discussed, and when the description is not particularly identified to relate to the present invention 1 or the present invention 2, the feature common to the inventions 1 and 2 is discussed.

The copolymer to be used for the medical adhesive composition of the present invention is obtained by copolymerizing a monomer mixture containing an acrylic acid alkyl ester having C4–C12 alkyl group, a (meth)acrylic acid and a methacrylic acid alkyl ester having C1–C4 alkyl group.

Examples of the above-mentioned acrylic acid alkyl ester having C4–C12 alkyl group include linear or branched alkyl group having 4 to 12 carbon atoms (e.g., butyl group, pentyl group, hexyl group, octyl group, nonyl group, decyl group, dodecyl group etc.). The acrylic acid alkyl ester to be used in the present invention is preferably 2-ethylhexyl acrylate, isooctyl acrylate and the like.

Examples of the above-mentioned methacrylic acid alkyl ester having C1–C4 alkyl group include a linear or branched alkyl group having 1 to 4 carbon atoms (e.g., methyl group, ethyl group, propyl group, butyl group, isobutyl group etc.). The methacrylic acid alkyl ester to be used in the present invention is preferably methyl methacrylate and the like.

The Present Invention 1

To afford an adhesive composition superior in the practical balance between adhesiveness and cohesiveness, the copolymer to be used for the adhesive composition is adjusted to have a gel-sol ratio of 35:65 to 55:45, preferably 40:60 to 50:50, and the weight average molecular weight of the sol portion is adjusted to 300,000 to 500,000, preferably 350,000 to 450,000, in the medical adhesive composition of the present invention 1. In addition, by adjusting the gel-sol ratio and the weight average molecular weight of the sol portion to the above ranges, skin contamination by the polymer having a low molecular weight can be prevented.

As used herein, by the "gel-sol ratio" in the present invention 1 is meant a ratio of the weight of the gel portion to the weight (weight of the sol portion) obtained by subtracting the weight of the gel portion from the initial weight of the copolymer. The weight of the gel portion is obtained by dissolving a predetermined amount of the obtained copolymer in toluene, filtering and drying a solvent insoluble component (gel portion), and measuring the weight of this component.

When the copolymer to be used for the medical adhesive composition of the present invention 1 contains a gel portion of a lower level than that defined by the above-mentioned gel-sol ratio, adhesion to the skin is improved, but the cohesiveness decreases, which in turn causes inconvenience such as adhesive residue and the like after peeling of the adhesive tape or sheet. In contrast, when the gel portion is contained at a higher level than that defined by the above-mentioned gel-sol ratio, the problem of adhesive residue is resolved but the adhesive layer has a higher cohesive force, thus increasing the resilience of the adhesive layer to the skin, which in turn causes inconvenience in that an adhesive tape or sheet falls from the skin and the like. When the weight average molecular weight of the sol portion is lower than 300,000, the polymer having a low molecular weight is produced in a greater amount, as a result of which an adhesive composition containing such polymer may unpreferably contaminate the skin. In contrast, when the weight average molecular weight of the sol portion is greater than 500,000, the skin is free of contamination but the adhesive layer has an increased cohesive force, which in turn causes inconvenience in that an adhesive tape or sheet unpreferably falls from the skin and the like.

In the medical adhesive composition of the present invention 1, the gel-sol ratio of the above-mentioned copolymer and the weight average molecular weight of the sol portion can be adjusted to fall within the above-mentioned range by controlling the composition (monomer charge ratio) of the acrylic acid alkyl ester, methacrylic acid alkyl ester and (meth)acrylic acid in the monomer mixture, or by changing the kind and amount of a chain transfer agent, polymerization temperature and the like. When the copolymerization is carried out by the emulsion polymerization to be mentioned later, the weight average molecular weight of the sol portion can be also controlled by adjusting the dripping speed of an emulsified monomer.

Specifically, 3 to 20 parts by weight, preferably 7 to 15 parts by weight, of a methacrylic acid alkyl ester, and 1 to 5 parts by weight, preferably 2 to 4 parts by weight, of a (meth)acrylic acid are charged in a monomer mixture, per 100 parts by weight of the acrylic acid alkyl ester.

When the methacrylic acid alkyl ester is charged in an amount of less than 3 parts by weight per 100 parts by weight of the acrylic acid alkyl ester, the obtained copolymer shows a lower glass transition temperature and improved adhesiveness, but lower cohesiveness to possibly leave an adhesive residue upon peeling in practical use. When the methacrylic acid alkyl ester is charged in an amount exceeding 20 parts by weight per 100 parts by weight of the acrylic acid alkyl ester, the obtained copolymer shows an increased glass transition temperature and lower adhesiveness. However, because the cohesiveness is increased, an adhesive tape or sheet is free of an adhesive residue upon peeling from the skin, shows lower adhesion to the skin and possibly causes an increased pain upon peeling due to stick-slip phenomenon and the like.

When the amount of the (meth)acrylic acid in a monomer mixture is less than 1 part by weight per 100 parts by weight of the acrylic acid alkyl ester, the obtained copolymer shows insufficient adhesiveness, whereas when it exceeds 5 parts by weight, the copolymer used for an adhesive composition may cause lower adhesiveness to the skin.

For the production of the above-mentioned copolymer, for example, lauryl mercaptan and the like are used as a chain transfer agent. The chain transfer agent is generally added in an amount of 0.02–0.1 part by weight, preferably 0.04 to 0.07 part by weight, per 100 parts by weight of the monomer mixture.

The polymerization temperature for the production of the above-mentioned copolymer is generally adjusted to 65 to 85° C., preferably 70 to 80° C.

The Present Invention 2

To afford an adhesive composition superior in the practical balance between adhesiveness and cohesiveness, the copolymer to be used for the adhesive composition is adjusted to have a gel fraction of 35 to 55%, and the swelling ratio of the gel portion adjusted to 50 to 90 times.

As used herein, the "gel fraction" in the present invention 2 is calculated as a proportion (unit: %) of the weight of the gel portion relative to the initial weight of the copolymer (weight of the gel portion+weight of the sol portion). The weight of the gel portion is obtained by dissolving a predetermined amount of the obtained copolymer in toluene, filtering, drying a solvent insoluble component (gel portion) and measuring the weight thereof.

The "swelling ratio of the gel portion" in the present invention 2 is calculated and expressed in a "swelling ratio" (unit: times) of the weight before drying (solvent+gel portion) to that after drying (gel portion), which is obtained by dissolving a predetermined amount of the obtained copolymer in toluene and filtering and measuring the weight, thereafter drying the gel and measuring the weight.

To be specific, the above-mentioned copolymer to be used for the present invention 2 shows a gel fraction of 35 to 55% and swelling ratio of the gel portion of 50 to 90 times, preferably a gel fraction of 40 to 50% and swelling ratio of the gel portion of 60 to 80 times. When the gel fraction is lower than 35% and the swelling ratio of the gel portion is higher than 90 times, the adhesive layer shows an improved skin adhesiveness but lower cohesiveness, which in practice causes inconvenience such as adhesive residue and the like. When the gel fraction is higher than 55% and the swelling ratio of the gel portion is lower than 50 times, the adhesive composition shows lower adhesiveness, which may possibly cause inconvenience in that the adhesive tape or sheet falls off from the skin and the like.

In the medical adhesive composition of the present invention 2, the gel fraction and the swelling ratio of the gel portion of the copolymer can be adjusted to fall within the above-mentioned ranges by changing the charge amount of monomers to be subjected to copolymerization of an acrylic acid alkyl ester, a methacrylic acid alkyl ester and a (meth)acrylic acid, or by changing the amount of a chain transfer agent, polymerization temperature and the like. When the copolymerization is carried out by the emulsion polymerization to be mentioned later, the swelling ratio of the gel portion can be also controlled by adjusting the dripping speed of an emulsified monomer.

Specifically, 3 to 20 parts by weight, preferably 7 to 15 parts by weight, of a methacrylic acid alkyl ester, and 1 to 5 parts by weight, preferably 2 to 4 parts by weight, of a (meth)acrylic acid are charged per 100 parts by weight of the acrylic acid alkyl ester, in a monomer mixture, which mixture is then copolymerized to give a copolymer.

When the methacrylic acid alkyl ester is charged in an amount of less than 3 parts by weight per 100 parts by weight of the acrylic acid alkyl ester, the obtained copolymer shows a lower glass transition temperature and improved adhesiveness, but lower cohesiveness. When such adhesive composition is used for an adhesive layer of an adhesive tape or sheet, therefore, an adhesive residue may be caused upon peeling. When the methacrylic acid alkyl ester is charged in an amount exceeding 20 parts by weight per 100 parts by weight of the acrylic acid alkyl ester, the obtained copolymer shows an increased glass transition temperature, lower adhesiveness and improved cohesiveness. When such adhesive composition is used for an adhesive layer of an adhesive tape or sheet, therefore, the adhesive tape or sheet is free of an adhesive residue upon peeling from the skin, shows lower adhesion to the skin and possibly causes an increased pain upon peeling due to a stick-slip phenomenon and the like.

When, in the production of the above-mentioned copolymer, the amount of the (meth)acrylic acid in a monomer mixture is less than 1 part by weight per 100 parts by weight of the acrylic acid alkyl ester, the obtained copolymer shows insufficient adhesiveness, whereas when it exceeds 5 parts by weight, the copolymer used for an adhesive composition may unpreferably show lower adhesiveness to the skin.

For the production of the above-mentioned copolymer, for example, lauryl mercaptan and the like are used as a chain transfer agent. The chain transfer agent is added generally in an amount of 0.02–0.1 part by weight, preferably 0.04 to 0.07 part by weight, per 100 parts by weight of the monomer mixture.

The polymerization temperature in the production of the above-mentioned copolymer is generally adjusted to 65 to 85° C., preferably 70 to 80° C.

Emulsion Polymerization

The copolymer to be used for the above-mentioned present inventions 1 and 2 may be obtained by any polymerization method, with preference given to emulsion polymerization.

According to the emulsion polymerization to be employed in the present invention, an emulsifier (surfactant mentioned below), a chain transfer agent and a polymerization initiator are mixed with a monomer mixture in the proportion explained with respect to the above-mentioned present invention 1 and present invention 2 in an aqueous medium, and polymerized at the aforementioned polymerization temperature to give a water-dispersion type copolymer.

For emulsion polymerization in the present invention, for example, a conventionally known method such as batch polymerization, monomer feeding polymerization, seed polymerization, emulsified monomer feeding polymerization and the like are used, but the method is not limited to these.

For emulsion polymerization, the dispersion stability and polymerization stability of the monomer mixture is generally maintained in an aqueous medium by the action of a surfactant. Examples of the surfactant include anionic emulsifiers (e.g., sodium sulfosuccinate, ammonium lauryl sulfate, sodium polyoxyethylenealkyl phenyl ether sulfate etc.), nonionic emulsifiers (e.g., polyoxyethylene alkyl ether, polyoxyalkyl phenyl ether etc.), cationic emulsifiers (e.g., alkyltrimethylammonium chloride, lauryltrimethylammonium chloride etc.), and the like, or reactive emulsifiers wherein an unsaturated group (e.g., propenyl group, allyl group etc., radical polymerizable group) is added to those mentioned above, and the like, which may be used alone or in combination of two or more thereof. Particularly, anionic emulsifier, nonionic emulsifier and reactive emulsifier are preferable from the aspect of polymerization stability.

Examples of the polymerization initiator to be used for the above-mentioned emulsion polymerization include, but not limited to, persulfate whose use for emulsion polymerization is known, organic peracid compounds, redox initiators, azo initiators and the like.

Medical Adhesive Composition

The medical adhesive composition of the present invention may contain, as an optional component in addition to the above-mentioned copolymers, other components (additives) that substantially do not exert an adverse influence on the properties of the copolymer. Examples of such additives include any additive generally used in the field of medical adhesive compositions, such as terpene and petroleum tackifier resins, liquid components as a plasticizer (compatible with the above-mentioned copolymers) and the like.

Adhesive Tape or Sheet

The medical adhesive tape or sheet of the present invention is obtained by forming the medical adhesive composition of the present invention on the entirety or a part (in spots) of one surface of the substrate and the like to form an adhesive layer having a thickness of 10 to 100 μm, preferably 20 to 80 μm.

The above-mentioned adhesive layer may be formed by directly applying and drying an adhesive composition on a substrate, or by applying an adhesive composition on a release paper, drying and adhering the paper to a substrate.

The material of a substrate of an adhesive tape or sheet of the present invention may be, for example, but not limited to, plastic film (e.g., polyethylene, polypropylene, ethylene/vinyl acetate copolymer, polyester, polyvinyl chloride, polyurethane etc.), woven fabric, knitted fabric, nonwoven fabric, paper, metal foil, laminates thereof and the like.

The shape of the adhesive tape or sheet of the present invention is not particularly limited as long as it is employed for medical and sanitary materials and is appropriately processed to give adhesive plasters, surgical tapes, dressings, drapes and the like.

EXAMPLES

The present invention is explained in detail by referring to Examples. The Examples are mere exemplification of representative examples and do not limit the present invention in any way.

Example 1

Distilled water (94 parts by weight), a surfactant (0.88 part by weight, reactive emulsifier, manufactured by Kao Corporation: trade name LATEMUL S180A), 2-ethylhexyl acrylate (93 parts by weight), acrylic acid (2 parts by weight), methyl methacrylate (10 parts by weight), lauryl mercaptan as a chain transfer agent (0.05 part by weight) and ammonium persulfate as a polymerization initiator (0.1 part by weight) were admixed in a reaction vessel equipped with a condenser, a nitrogen induction tube, a thermometer and a stirrer and reacted for emulsified monomer feeding polymerization at a polymerization temperature of 70° C. for about 4.5 hr, followed by aging at 86° C. for 2 hr to complete the copolymerization, whereby a copolymer solution (adhesive composition) was obtained.

This adhesive composition was applied to a silicone-treated surface of a release paper such that the adhesive layer has a thickness of 40 μm and dried to form an adhesive layer. This copolymer solution was applied to one surface of a 38 μm PET film such that the adhesive layer has a thickness of 40 μm and dried to give an adhesive tape of the present invention.

The adhesive layer obtained in the above was used for the measurement (measurements 1, 2 and 5) of the gel-sol ratio, weight average molecular weight of the sol portion and the swelling ratio of the gel portion to be mentioned below.

The adhesive tape of the present invention obtained above was used for the adhesive force measurement and utility test (measurements 3, 4 and 6) to be mentioned below.

Examples 2 and 3

In the same manner as in Example 1 except that the composition of the monomer mixture and the amount of the chain transfer agent were changed as shown in Table 1, two kinds of adhesive tapes and adhesive layers were prepared.

Comparative Examples 1 to 4

In the same manner as in Example 1 except that the composition of the monomer mixture and the amount of the chain transfer agent were changed as shown in Table 2, four kinds of adhesive tapes and adhesive layers were prepared.

The compositions of the monomer mixtures used for the production of the copolymers of Examples 1 to 3 are shown in Table 1, and the compositions of the monomer mixtures in Comparative Examples 1–4 are shown in Table 2.

TABLE 1

| | | Examples | | |
|---|---|---|---|---|
| | | 1 | 2 | 3 |
| composition of monomer mixture (parts by weight) | 2-ethylhexyl acrylate | 93 | 90.5 | 98 |
| | acrylic acid | 2 | 2 | 2 |
| | methyl methacrylate | 10 | 12.5 | 5 |
| amount of chain transfer agent (parts by weight) | lauryl mercaptan | 0.05 | 0.05 | 0.05 |

TABLE 2

| | | Comparative Examples | | | |
|---|---|---|---|---|---|
| | | 1 | 2 | 3 | 4 |
| composition of monomer mixture (parts by weight) | 2-ethylhexyl acrylate | 103 | 93 | 88 | 98 |
| | acrylic acid | 2 | 2 | 2 | 2 |
| | methyl methacrylate | 0 | 10 | 15 | 5 |
| amount of chain transfer agent (part by weight) | lauryl mercaptan | 0.05 | 0.08 | 0.05 | 0.03 |

The measurement of the gel-sol ratio and the weight average molecular weight of the sol portion of the adhesive layers prepared in the above-mentioned Examples 1 to 3 and Comparative Examples 1, 3 and 4, and the adhesive force measurement and utility test (evaluation of skin adhesiveness, pain during peeling, adhesive residue after peeling and skin contamination) of the prepared adhesive tapes of the present invention were performed in the following manner. The measurement results thereof are shown in Table 3. The criteria of the utility test are as shown in Table 4.

Measurement 1: Gel-sol Ratio

A predetermined amount of an adhesive layer was stirred in toluene at an ambient temperature for 7 days, and a solvent insoluble component (gel portion) was filtered through a polytetrafluoroethylene membrane (manufactured by Nitto Denko Corp., NTF membrane) having an average pore size of 0.2 μm, dried and measured for the weight (weight of the gel portion). The weight of the sol portion was obtained by subtracting the weight of the gel portion from the initial weight of the copolymer (weight of sol portion). Using these weights, the gel-sol ratio was determined.

Measurement 2: Weight Average Molecular Weight of Sol Portion

About 10 mg of the adhesive layer was dissolved by immersion in 10 ml of THF for 12 hours or longer. This solution was filtered through a 0.2 μm membrane filter. The filtrate was subjected to a GPC method and the weight average molecular weight of the sol portion was calculated by polystyrene conversion.

The analysis equipment used for the GPC method was HLC8120GPC (manufactured by TOSOH).

Measurement 3: Adhesive Force of Adhesive Tape

The adhesive tapes obtained in Examples and Comparative Examples were cut into 19 mm width in size and cast in a 35° C., 30% RH atmosphere, and the adhesive layer was press-adhered to a phenol resin laminate board with a 2 kg rubber roller. After 20 minutes, the layer was peeled off and the stress upon peeling at 300 mm/min and angle 90° was taken as the adhesive force (unit: N/19 mm).

Measurement 4: Utility Test

An adhesive tape cut in the size of width 15 mm and length 40 mm was adhered to the skin surface of medial forearm of volunteers. After 3 hours from the adhesion, skin adhesiveness, pain during peeling, adhesive residue after peeling and skin contamination were evaluated. The criteria of each test item were as shown in Table 4.

TABLE 3

|  | Examples | | | Comparative Examples | | |
| --- | --- | --- | --- | --- | --- | --- |
|  | 1 | 2 | 3 | 1 | 3 | 4 |
| gel-sol ratio | 45:55 | 39:61 | 49:51 | 54:46 | 22:78 | 63:37 |
| weight average molecular weight of sol portion | 330,000 | 390,000 | 370,000 | 240,000 | 370,000 | 340,000 |
| adhesive force (N/19 mm) | 9.3 | 11.8 | 9.3 | 6.0 | 11.5 | 6.5 |
| skin adhesiveness | ○ | ○ | ○ | Δ | Δ | x |
| pain during peeling | Δ | Δ | ○ | x | x | ○ |
| adhesive residue after peeling | ○ | ○ | ○ | Δ | ○ | ○ |
| skin contamination after peeling | ○ | ○ | ○ | x | ○ | ○ |

TABLE 4

| skin adhesiveness | ○: very strong sense of adhesion |
|  | Δ: moderate sense of adhesion |
|  | x: weak sense of adhesion |
| pain on peeling | ○: no pain |
|  | Δ: slight pain but no problem |
|  | x: painful |
| adhesive residue after peeling | ○: no adhesive residue |
|  | Δ: slight adhesive residue |
|  | x: much adhesive residue |
| skin contamination after peeling | ○: same as before adhesion |
|  | Δ: slightly tacky |
|  | x: tacky |

As shown in Table 3, the medical adhesive compositions of Examples 1–3 having a gel-sol ratio and an average molecular weight of the sol portion within the range defined in the present invention showed a superior balance between the adhesiveness and cohesiveness and superior properties in practical use. In contrast, those of Comparative Examples 1, 3 and 4, which had a gel-sol ratio and an average molecular weight of the sol portion outside the range defined in the present invention, showed poor balance between the adhesiveness and cohesiveness.

In addition, the gel fraction and the swelling ratio of the gel portion of the copolymers prepared in the above-mentioned Examples 1–3 and Comparative Examples 2–4 and the utility test (evaluation of skin adhesiveness, pain during peeling, adhesive residue after peeling and skin contamination) of the adhesive sheet comprising these copolymers as adhesive composition were performed in the following manner. The results thereof are shown in Table 5. The criteria of each item of the utility test shown in Table 5 are the same as those shown in Table 4.

For reference, the relationship between the gel fraction and the swelling ratio of the gel portion obtained with the copolymers of Examples 1 to 3 and Comparative Examples 2 to 4 is shown in FIG. 1.

Measurement 5: Gel Fraction and Swelling Ratio of Gel Portion

A predetermined amount of a copolymer was stirred in toluene at an ambient temperature for 7 days, and a solvent insoluble component (gel portion) was filtered through a polytetrafluoroethylene membrane (manufactured by Nitto Denko Corp., NTF membrane) having an average pore size of 0.2 μm, dried and weighed (weight of the gel portion containing toluene). The gel was dried and the weight thereof (weight of the gel portion) was measured. The percentage of the weight of the gel portion relative to the initial weight of the copolymer was calculated as a gel fraction (unit: %). In addition, the weight ratio of the gel portion containing toluene relative to the weight of the gel portion was calculated to show the swelling ratio of the gel portion (unit: times).

Measurement 6: Utility Test

An adhesive tape cut in the size of width 15 mm and length 40 mm was adhered to the skin surface of medial forearm of volunteers. After 3 hours from the adhesion, skin adhesiveness, pain during peeling, adhesive residue after peeling and skin contamination were evaluated. The criteria of each test item in Table 5 were the same as those shown in Table 4.

TABLE 5

|  | Examples | | | Comparative Examples | | |
| --- | --- | --- | --- | --- | --- | --- |
|  | 1 | 2 | 3 | 2 | 3 | 4 |
| gel fraction (%) | 45 | 39 | 49 | 33 | 22 | 63 |
| swelling ratio of gel portion (times) | 62 | 70 | 66 | 97 | 150 | 45 |
| adhesion to skin | ○ | ○ | ○ | ○ | Δ | x |
| pain upon peeling | Δ | Δ | ○ | Δ | x | ○ |

TABLE 5-continued

| | Examples | | | Comparative Examples | | |
|---|---|---|---|---|---|---|
| | 1 | 2 | 3 | 2 | 3 | 4 |
| adhesive residue after peeling | ○ | ○ | ○ | x | ○ | ○ |
| skin contamination after peeling | ○ | ○ | ○ | x | ○ | ○ |

FIG. 1 clearly reveals the correlation between the gel fraction and the swelling ratio of the gel portion.

In addition, the results shown in Table 5 reveal that the medical adhesive compositions of Examples 1 to 3 having a gel fraction and a swelling ratio of the gel portion within the range defined in the present invention showed superior balance between adhesiveness and cohesiveness and superior properties in practical use. In contrast, the medical adhesive compositions of Comparative Examples 2 to 4 having one or both of the gel fraction and the swelling ratio of the gel portion outside the range defined in the present invention showed poor balance between adhesiveness and cohesiveness.

From the foregoing, it is evident that the medical adhesive composition having the constitution of the present invention is superior in the balance between adhesiveness that affords sufficient adhesion to the skin when used as an adhesive tape or sheet for the skin, and cohesiveness that prevents adhesive residue upon peeling. Accordingly, the medical adhesive composition of the present invention can be used as an adhesive layer of an adhesive tape or sheet preferably used for various medical and sanitary uses as adhesive plasters, dressings, drapes and the like.

This application is based on Japanese Patent Application No. 2001-253579 filed in Japan, the contents of which are hereby incorporated by reference. All of the references cited herein, including patents, patent applications, and publications, are hereby incorporated in their entireties by reference.

What is claimed is:

1. A medical adhesive composition comprising a copolymer obtained by copolymerization of a monomer mixture containing an acrylic acid alkyl ester having C4–C12 alkyl group, a (meth)acrylic acid, and a methacrylic acid alkyl ester having C1–C4 alkyl group, which mixture is free of a multifunctional monomer having two or more unsaturated double bonds in a molecule, wherein the copolymer has a gel-sol ratio of 35:65 to 55:45 and a weight average molecular weight of the sol portion of 300,000 to 500,000.

2. The composition according to claim 1, wherein the copolymerization is carried out by emulsion polymerization.

3. The composition according to claim 2, wherein the emulsion polymerization is carried out in the presence of an emulsifier, a chain transfer agent and a polymerization initiator.

4. The composition according to claim 1, wherein the monomer mixture comprises 1 to 5 parts by weight of the (meth)acrylic acid and 3 to 20 parts by weight of the methacrylic acid alkyl ester, per 100 parts by weight of the acrylic acid alkyl ester.

5. An adhesive tape or sheet comprising a substrate and an adhesive layer comprising the medical adhesive composition according to claim 1 formed on one surface of the substrate in a thickness of 10 to 100 µm.

6. A medical adhesive composition comprising a copolymer obtained by copolymerization of a monomer mixture containing an acrylic acid alkyl ester having C4–C12 alkyl group, a (meth)acrylic acid, and a methacrylic acid alkyl ester having C1–C4 alkyl group, which mixture is free of a multifunctional monomer having two or more unsaturated double bonds in a molecule, wherein the copolymer has a gel fraction of 35 to 55% and a swelling ratio of a gel portion of 50 to 90 times.

7. The composition according to claim 6, wherein the copolymerization is carried out by emulsion polymerization.

8. The composition according to claim 7, wherein the emulsion polymerization is carried out in the presence of an emulsifier, a chain transfer agent and a polymerization initiator.

9. The composition according to claim 6, wherein the monomer mixture comprises 1 to 5 parts by weight of the (meth)acrylic acid and 3 to 20 parts by weight of the methacrylic acid alkyl ester, per 100 parts by weight of the acrylic acid alkyl ester.

10. An adhesive tape or sheet comprising a substrate and an adhesive layer comprising the medical adhesive composition according to claim 6 formed on one surface of the substrate in a thickness of 10 to 100 µm.

* * * * *